United States Patent [19]
Koelman et al.

[11] Patent Number: 5,922,611
[45] Date of Patent: Jul. 13, 1999

[54] DETERMINING A PARAMETER IN A PHYSICAL SYSTEM

[75] Inventors: Johannes Maria Vianney Antonius Koelman; Andre De Kuijper, both of Rijswijk; Robert Karl Josef Sandor, The Hague, all of Netherlands

[73] Assignee: Shell Oil Company, Houston, Tex.

[21] Appl. No.: 08/847,725

[22] Filed: Apr. 28, 1997

[51] Int. Cl.$^6$ .......................... G01N 27/00; G01N 33/24
[52] U.S. Cl. .............................. 436/149; 436/25; 436/28; 436/29; 436/31; 436/150
[58] Field of Search ................................. 436/25, 28, 29, 436/31, 149, 150, 183

[56] References Cited

PUBLICATIONS

M.H. Waxman etal, *J. Petrol. Technol.* 1974, 26, 213–225.
W.H. Fertl *Oil Gas J.* 1978, 76, 73–76.
L.J. Volk etal. *J. Petrol. Techol.* 1980, 32, 865–867.
K.K. Mohanty etal. *Chem. Eng. Sci.* 1982, 37, 905–924.
M.H. Waxman etal. *Proc.—Electrochem. Soc.* 1985, 85–8, 209–223.
F.D. Agterberg etal. *Pap.—Geol. Surv. Can.* 1985, 85–1B, 451–458.
E. Dykesteen etal. *J. Phys. E.* 1985, 18, 540–544.
W.H. Fertl *J. Petrol. Technol.* 1987, 39, 175–194.
W.M. Waxman etal. *Proc. World Pet. Congr.* 1987, 12$^{th}$, 287–294.
S. Zhao etal. *Jisuanji Yu Yingyong Huaxue* 1987, 4, 307–312.
S.A. Rackley etal. *SPE Farm. Eval.* 1989, 4, 363–370.
S.K. Park etal. *Ground Water* 1989, 27, 786–792.
R.Ehrlich etal. *AAPG Bull.* 1991, 75, 1579–1592.
R.E. Maute etal. *J. Petrol. Technol,* 1992, 44, 103–107.
J.C. Harris etal. *Proc. Annu. SouthWest. Pet. Short Course* 1992, 151–156.
W.M. Waxman etal. *Proc. World Pet. Congr.* 1987, 12$^{th}$, 287–294.
Spalburg, M. R., "The Effective medium theory used to derive conductivity equations for clean and shaly hydrocarbon bearing reservoirs," paper at the 11th European Formation Evaluation Symposium, Oslo (1988).
Clavier, C., Coates, G., and Dumanoir, J., "The theoretical and experimental bases for the dual water model for the interpretation of shaly sands" Soc. Pet. Engrs. J. 24 153 (1984).
Poupon, A. and Levenaux, J., "Evaluation of water saturations in shaly formations," Trans. SPWLA 12th Ann. Logging Symp. paper O1–2 (1971) Abstract only.
Simandous, P., "Dielectric measurements on porous media: application to the measurement of water saturations: study of the behaviour of argillaceous formations," Revue de l'institute Francais du Petrol, 18 suppl., 193 (1963).
Waxman, M.H., and Smits, L.J.M., "Electrical conductivities in oil–bearing shaly sands," SPE paper 1863–A presented at the 42nd Annual Fall Meeting, Houston, Oct. 1–4, 1967.
Archie, G. E., "The electrical resistivity log as an aid in determining some reservoir characteristics," Trans AIME, 42, 54 (1942).

*Primary Examiner*—Arlen Soderquist

[57] ABSTRACT

A method of determining a parameter of a physical model representing the electrical behavior of a composition is provided. The method comprises defining said model by a relationship between the electrical properties of the composition, a plurality of physical variables of the composition and said parameter, and measuring an electrical property of the composition. A sample which is representative for said composition is selected, and an electrical property of the sample is measured for various magnitudes of at least one of said physical variables. An incoherence function is selected, defining a difference between the measured electrical properties and the electrical properties as calculated from said relationship, said incoherence function being such that independent measurements are weighted in dependence of their accuracy. The parameter is determined by minimization of the incoherence function.

17 Claims, No Drawings

DETERMINING A PARAMETER IN A PHYSICAL SYSTEM

FIELD OF THE INVENTION

The present invention relates to a method of determining a parameter in a physical system representing the electrical behavior of a composition. The method can for example be applied in well-logging whereby the objective is to determine a quantity of a fluid, such as water, brine or hydrocarbon, in an earth formation in order to assess whether the formation can be exploited economically.

BACKGROUND TO THE INVENTION

In the art of well-logging, physical models are generally applied to represent the electrical behavior of the earth formation. From the well-log results and the physical model, the content of a component of the earth formation is then determined.

A known method of determining parameters of such physical model is disclosed in "Electrical conductivities in oil-bearing shaly sands", Waxman M. H., and Smits L. J. M., SPE paper 1863-A presented at the 42nd Annual Fall Meeting, Houston, Oct. 1–4, 1967. This paper discloses a method of determining a parameter of a physical model representing the electrical behavior of an earth formation, consisting of defining said model by a relationship between the conductivity of the formation, a plurality of physical variables of the formation and said parameter, selecting a sample which is representative for said formation and measuring the electrical conductivity of the sample for various magnitudes of the physical variables, and determining said parameter by applying the selected relationship to the measured conductivities of the sample.

In this known method the model, which is generally referred to as the Waxman-Smits model, is defined by the relationship:

$$C_t = \frac{1}{G^*}\left(C_w + \frac{BQ_v}{S_w}\right)$$

wherein;

$C_t$=the conductivity of the partially brine saturated formation represented by the sample $C_w$=the conductivity of brine present in the formation;

$S_w$=the water saturation in the pore space (0 . . . 1), which equals $1-=S_o$ where $S_o$ denotes the hydrocarbon saturation;

B=the equivalent conductance of sodium clay-exchange cations as a function of $C_w$ and temperature;

$Q_v$=the cation exchange capacity per unit pore volume;

$G^*$=a formation factor of the formation represented by the sample;

$G^*$ is represented as:

$$G^* = \phi^{-m^*} S_w^{-n^*}$$

wherein $\phi$=the pore space in the formation;

$m^*$=a parameter to be determined, in the form of the cementation exponent;

$n^*$=a parameter to be determined, in the form of the saturation exponent.

The parameters $m^*$ and $n^*$ characterize the response of the conductivity of the earth formation subject to changes in physical variables such as $\phi$ and $S_w$. In the known method these parameters are determined in a mutually independent way, namely:

by using conductivity measurements in a non-hydrocarbon bearing zone in the earth formation or with laboratory conductivity measurements on a plurality of fully brine saturated samples; $m^*$ can be determined from the relation between $\log(C_t^{-1})$ and $\log(\phi)$ or $\log(C_w \cdot C_t^{-1})$ and $\log(\phi)$, respectively; and by using laboratory conductivity measurements on a plurality of partially brine saturated samples $n^*$ can be determined from the relation between $$\log\left(\frac{C_t(S_w \equiv 1)}{C_t(S_w)} \frac{(C_w + BQ_v/S_w)}{(C_w + BQ_v)}\right)$$

and $\log(S_w)$.

The results achieved with this known method are not always sufficiently accurate, probably because the parameters are determined in a non-optimal manner.

It is an objective of the invention to provide an improved method of determining a parameter of a physical model representing the electrical behavior of a composition.

SUMMARY OF THE INVENTION

These and other objectives are achieved by a method comprising the steps of:

defining said model by a relationship between the electrical properties of the composition, a plurality of physical variables of the composition and said parameter;

measuring an electrical property of the composition;

selecting a sample which is representative for said composition and measuring an electrical property of the sample for various magnitudes of at least one of said physical variables;

selecting an incoherence function defining a difference between the measured electrical properties of the composition and the sample, and the electrical properties of the composition and the sample as determined from said relationship, said incoherence function being such that independent measurements are weighted in dependence of their accuracy; and determining said parameter by minimization said incoherence function.

Advantageously a plurality of said parameters are determined simultaneously in minimizing said incoherence function, each parameter being represented in said relationship.

By minimizing the incoherence function each parameter is determined in a manner that all experimental data, both from in-situ measurements of the composition and from laboratory measurements on samples representative for the composition, are taken into account in a weighted manner, i.e. in dependence of their respective accuracies. For example, in case the composition forms an earth formation, less accurate well-log measurements are taken into account in the incoherence function with less weight than accurate sample measurements. It is thereby achieved that the parameters are determined with increased accuracy resulting in a physical model, and applications thereof, of increased accuracy.

Preferably, said incoherence function is selected such that independent measurements of substantially equal accuracy are substantially equally represented therein.

DESCRIPTION OF PREFERRED EMBODIMENTS

Models which the present invention can be applied include, but are not limited to: the Waxman-Smits model, the Archie model, the Poupon-Leveaux model, the Simandoux model, the Dual-Water model of Clavier-Coates-Dumanoir, and the effective medium model of Spalburg.

Suitably said relationship is selected to include the conductivity of the composition and a plurality of composition parameters including, for each component in the composition, physical parameters representing the conductivity and the volume fraction of the component, said relationship being such that the components are substantially equally represented in said relationship by means of said physical parameters.

For example, the relationship can be selected as:

$$(\sigma_{eff}-\sigma_0) \cdot (L\sigma_{eff}+(1-L)\sigma_0)^{-1} = \Sigma\phi_k(\sigma_k-\sigma_0) \cdot (L\sigma_k+(1-L)\sigma_0)^{-1}$$

wherein $\sigma_0$ represents an auxiliary parameter in the form of a conductivity tensor k=1 ... N, N being the number components in the composition $\sigma_{eff}$ represents the conductivity tensor of the sample $\sigma_k$ represents the conductivity tensor of component k $\phi_k$ represents the volume fraction of component k L represents a depolarization tensor.

Advantageously said auxiliary parameter is selected to be:

$$\sigma_0 = \Sigma h_k \sigma k$$

wherein $h_k$ represents a mixing coefficient tensor pertaining to component k.

Preferably each mixing coefficient is selected as $$h_k = \lambda_k \phi_k^{v} (\Sigma \lambda_n \phi_n^{v})^{-1}$$

wherein k, n=1 ... N, N being the number components in said plurality of components $\lambda_k$ represents a percolation rate tensor pertaining to component k $\phi_k$ represents the volume fraction of component k $v_{k,n}$ represents a percolation exponent pertaining to component k, n.

The invention will be described hereinafter in more detail and by way of example.

Consider a set of measurements made on an earth formation which essentially consists of rock, brine, clay, and hydrocarbons. The measurements include:

A) logging data on a water-bearing interval in the formation, the data consisting essentially of conductivity and porosity measurements under known $C_w$, $S_w$(=1), and T conditions;

B) logging data on an interval in said formation susceptible of being hydrocarbon-bearing, which data essentially consist of conductivity and porosity measurements under known $C_w$, and T conditions;

C) laboratory data on core plugs representative for said formation, the data consisting essentially of conductivity, porosity, and $Q_v$ measurements under controlled $S_w$, $C_w$, and T conditions;

Then, from the laboratory data, a standard correlation between the porosity and $Q_v$ can be made, providing $Q_v$ information along with the logging data. As saturation model the Waxman-Smits model referred to in the description of the prior art method, will be used, i.e.:

$$C_t = \frac{1}{G^*}\left(C_w + \frac{BQ_v}{S_w}\right)$$

For the data mentioned under points A) and C) an incoherence function P(m*n*) is defined as follows:

$$P(m^*, n^*) := \sum_{i=1}^{N} w_i \left(\frac{K_{t,i} - C_{t,i}}{K_{t,i}}\right)^2 + \sum_{j=1}^{M} w_j \left(\frac{K_{t,i} - C_{t,i}}{K_{t,i}}\right)^2$$

wherein i=1 ... N, N=the total number of independent measurements referred to under A);

$w_i$=the weight attributed to the i-th measured conductivity of the rock;

$C_{t,i}$=the i-th calculated conductivity of the rock whose value depends on m* and n*;

$K_{t,i}$=the i-th measured conductivity of the rock;

j=1 ... M, M=the total number of measurements referred to under C);

$w_j$=the weight attributed to the j-th measured conductivity of the rock;

$C_{t,j}$=the j-th calculated conductivity of the rock whose value depends on m* and n*;

$K_{t,j}$=the j-th measured conductivity of the rock;

m*=a parameter in the form of the cementation exponent, to be determined;

n*=a parameter in the form of the saturation exponent, to be determined;

The weights are chosen proportional to the inverse of the estimated accuracy variation of the measurement. The values of m* and n* are determined by minimizing P(m*,n*) using a multi-dimensional down-hill-simplex method, which is an iterative mathematical method well-known to those skilled in the art.

The resulting values for m* and n* can then be used in the Waxman-Smits model to solve for $S_w$ given the data referred to under B), thus providing the water-saturation (hence also the hydrocarbon saturation) in the earth formation.

The incoherence function can be, for example, of the form:

$$\sum_{i=1}^{N} w_i F\left(\frac{G(X_i) - G(Y_i)}{H(X_i)}\right)$$

wherein i=1 ... N, N being the number of physical measurements, $X_i$ represents the measured electrical property, $Y_i$ represents the calculated electrical property, G and H represent functions of the electrical property ($H(X_i)>0$)

F represents a function with $X \neq 0[F(X)>F(0)$, $w_i$ represents the weight attributed to the physical measurement ($w_i \geq 0$)

In another embodiment, the function F can be defined as:

$F(X)=|X|^\alpha, \alpha \in R, \alpha>)$ $G(X)=X^\beta, \beta \in R, \beta \neq 0$ $H(X)=1$ or $H(X)=G(X)$ The incoherence function could alternatively be of the form:

$$\sum_{i=1}^{N} w_i F\left(\frac{G(X_i) - G(Y_i)}{H(X_i)}\right)$$

wherein i=1 ... N, N being the number of physical measurements, $X_i$ represents the measured electrical property, $Y_i$ represents the calculated electrical property, $w_i$ represents the weight attributed to the physical measurement ($w_i \geq 0$).

The incoherence function could alternatively be of the form:

$$\sum_{i=1}^{N} w_i \left(\frac{X_i - Y_i}{X_i}\right)^2$$

wherein i=1 . . . N, N being the number of physical measurements, $X_i$ represents the measured electrical property, $Y_i$ represents the calculated electrical property, $w_i$ represents the weight attributed to the physical measurement ($w_i \geq 0$)

We claim:

1. A method of determining a parameter of a physical model representing the electrical behavior of a composition, the method comprising:

defining said model by a relationship between the electrical properties of the composition, a plurality of physical variables of the composition and said parameter;

measuring an electrical property of the composition and determining a weighting factor reflective of the measurement accuracy;

selecting a sample which is representative for said composition and measuring an electrical property of the sample for various magnitudes of at least one of said physical variables and determining a weighting factor reflective of the accuracy of the measurements;

selecting an incoherence function defining a difference between the measured electrical properties and the electrical properties as calculated from said relationship, said incoherence function being such that independent measurements include the determined weighting factors; and determining said parameter by minimization of said incoherence function.

2. The method of claim 1 wherein the step of determining said parameter by minimization of said incoherence function includes an iterative process.

3. The method of claim 1 wherein a plurality of said parameters are determined simultaneously by minimizing the incoherence function, each parameter being represented in said relationship.

4. The method of claim 1 wherein said incoherence function is selected such that independent measurements of substantially equal accuracy are substantially equally represented therein.

5. The method of claim 1 wherein the electrical properties of the composition as defined in said relationship and the measured electrical property of the sample are selected from the conductivity, the resistivity and the membrane potential.

6. The method of claim 1 wherein the measured electrical property of the composition is selected from the conductivity and the resistivity.

7. The method of claim 1 wherein said composition includes a fluid and the model forms a saturation model for the fluid in the composition.

8. The method of claim 7, wherein said composition comprises an earth formation, and the model forms a saturation model for a selected one of brine and hydrocarbon fluid contained in the formation.

9. The method of claim 1 wherein said relationship is selected to include the conductivity of the composition and a plurality of composition parameters including, for each component in the composition, physical parameters representing the conductivity and the volume fraction of the component, said relationship being such that the components are substantially equally represented in said relationship by means of said physical parameters.

10. The method of claim 9, wherein the relationship is selected as:

$$(\sigma_{eff} - \sigma_0) \cdot (L\sigma_{eff} + (1-L)\sigma_0)^{-1} = \Sigma_k (\sigma_k - \sigma_0) \cdot (L\sigma_k + (1-L)\sigma_0)^{-1}$$

wherein $\sigma_0$ represents an auxiliary parameter in the form of a conductivity tensor k=1 . . . N, N being the number components in the composition $\sigma_{eff}$ represents the conductivity tensor of the sample $\sigma_k$ represents the conductivity tensor of component k $\phi_k$ represents the volume fraction of component k L represents a depolarization tensor.

11. The method of claim 1 wherein said model is selected from the group consisting of Waxman-Smits model, the Archie model, the Poupon-Leveaux model, the Simandoux model, the Dual-Water model of Clavier-Coates-Dumanoir, and the effective medium model of Spalburg.

12. The method of claim 1 wherein the step of determining said parameter by minimization of said incoherence function is carried out in a minimization algorithm.

13. The method of claim 1 wherein said incoherence function is monotonically increasing with the deviation between the measured electrical properties and the calculated electrical properties.

14. The method of claim 1 wherein said incoherence function is of the form:

$$\sum_{i=1}^{N} w_i F\left(\frac{G(X_i) - G(Y_i)}{H(X_i)}\right)$$

wherein i=1 ... N, N being the number of physical measurements, $X_i$ represents the measured electrical property, $Y_i$ represents the calculated electrical property, G and H represent functions of the electrical property ($H(X_i) > 0$)

F represents a function with $X \neq 0 [F(X) > F(0)]$, $w_i$ represents the weight attributed to the physical measurement ($w_i \geq 0$).

15. The method of claim 14, wherein $F(X) = |X|^\alpha, \alpha \in R, \alpha > 0$ $G(X) = X^\beta, \beta \in R, \beta \neq 0$ $H(X) = 1$ or $H(X) = G(X)$.

16. The method of claim 1 wherein said incoherence function is of the form:

$$\sum_{i=1}^{N} w_i(X_i - Y_i)^2$$

wherein
- i=1 ... N, N being the number of physical measurements,
- $X_i$ represents the measured electrical property,
- $Y_i$ represents the calculated electrical property,
- $w_i$ represents the weight attributed to the physical measurement ($w_i$ 24 0).

17. The method of claim 1, wherein said incoherence function is of the form:

$$\sum_{i=1}^{N} w_i\left(\frac{X_i - Y_i}{X_i}\right)^2$$

wherein i=1 ... N, N being the number of physical measurements,
- $X_i$ represents the measured electrical property,
- $Y_i$ represents the calculated electrical property,
- $w_i$ represents the weight attributed to the physical measurement ($w_i$24 0).

* * * * *